United States Patent
Mineta et al.

(10) Patent No.: US 11,906,419 B2
(45) Date of Patent: Feb. 20, 2024

(54) CORROSIVENESS PREDICTION DEVICE AND METHOD

(71) Applicant: Nippon Telegraph and Telephone Corporation, Tokyo (JP)

(72) Inventors: Shingo Mineta, Musashino (JP); Shota Oki, Musashino (JP); Mamoru Mizunuma, Musashino (JP); Masayuki Tsuda, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 301 days.

(21) Appl. No.: 17/604,833

(22) PCT Filed: May 10, 2019

(86) PCT No.: PCT/JP2019/018688
§ 371 (c)(1),
(2) Date: Oct. 19, 2021

(87) PCT Pub. No.: WO2020/230183
PCT Pub. Date: Nov. 19, 2020

(65) Prior Publication Data
US 2022/0196541 A1    Jun. 23, 2022

(51) Int. Cl.
*G01N 17/02* (2006.01)
*G01N 17/00* (2006.01)
*G01N 33/20* (2019.01)

(52) U.S. Cl.
CPC .......... *G01N 17/02* (2013.01); *G01N 17/002* (2013.01); *G01N 17/006* (2013.01); *G01N 33/20* (2013.01)

(58) Field of Classification Search
CPC .... G01N 17/02; G01N 17/002; G01N 17/006; G01N 33/20; G01N 27/26; G01N 33/24
See application file for complete search history.

(56) References Cited

U.S. PATENT DOCUMENTS

| | | | |
|---|---|---|---|
| 2010/0163469 A1* | 7/2010 | Wan | G05D 21/02 210/96.1 |
| 2014/0210494 A1* | 7/2014 | Ghods | G01N 27/026 324/700 |

(Continued)

OTHER PUBLICATIONS

Satomi Tsunoda et al., *Some Problems for Evaluating Soil Aggressivity*, Boshoku Gijutsu, vol. 36, 1987, pp. 168-177.

*Primary Examiner* — Alvaro E Fortich
(74) *Attorney, Agent, or Firm* — Workman Nydegger

(57) ABSTRACT

A corrosion prediction device that predicts corrosion indicating the degree to which a metal will corrode in an environment, the device including a storage unit which stores a soil sample that simulates the environment and an electrode unit and has a function of repeatedly performing water supply and drainage with respect to the soil sample; the electrode unit including at least one type of metal pieces; a measurement unit that measures, based on change in water content in the environment in one cycle, a corrosion rate of the metal pieces or a value proportional to the corrosion rate of the metal pieces during the change; a calculation unit that integrates the corrosion rate or a value proportional to the corrosion rate over time and calculates an amount of corrosion or a value proportional to the amount of corrosion; and a prediction unit that determines a constant value of K of the power law and a constant value of n of the power law using a difference between the amounts of corrosion or the values proportional to the amounts of corrosion in different periods.

3 Claims, 12 Drawing Sheets

(56) References Cited

U.S. PATENT DOCUMENTS

| | | | |
|---|---|---|---|
| 2015/0038750 A1* | 2/2015 | Weiss | C25B 1/26 422/186 |
| 2015/0185133 A1* | 7/2015 | Murray | G01N 17/04 205/775.5 |
| 2018/0238820 A1* | 8/2018 | Ghods | G01N 27/026 |

* cited by examiner $R_{s1}, R_{s2}$ : RESISTANCE IN SOIL AND ANOTHER RESISTANCE COMPONENT
$R_{ct}$ : CHARGE TRANSFER RESISTANCE
$C_{dl}$ : ELECTRIC DOUBLE LAYER CAPACITANCE
$C_s$ : CAPACITANCE COMPONENT IN SOIL $R_{s1}, R_{s2}$ : RESISTANCE IN SOIL AND ANOTHER RESISTANCE COMPONENT
$R_{ct}$ : CHARGE TRANSFER RESISTANCE
$C_{dl}$ : ELECTRIC DOUBLE LAYER CAPACITANCE
$C_s$ : CAPACITANCE COMPONENT IN SOIL

Fig. 8(a)

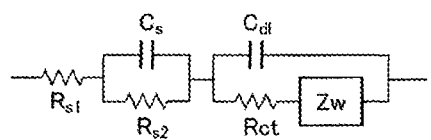

$R_{s1}, R_{s2}$ : RESISTANCE IN SOIL AND ANOTHER RESISTANCE COMPONENT
$R_{ct}$ : CHARGE TRANSFER RESISTANCE
$C_{dl}$ : ELECTRIC DOUBLE LAYER CAPACITANCE
$C_s$ : CAPACITANCE COMPONENT IN SOIL
$Z_w$ : WARBURG IMPEDANCE

Fig. 8(b)

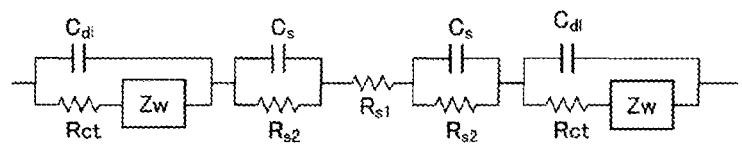

$R_{s1}, R_{s2}$ : RESISTANCE IN SOIL AND ANOTHER RESISTANCE COMPONENT
$R_{ct}$ : CHARGE TRANSFER RESISTANCE
$C_{dl}$ : ELECTRIC DOUBLE LAYER CAPACITANCE
$C_s$ : CAPACITANCE COMPONENT IN SOIL
$Z_w$ : WARBURG IMPEDANCE

CORROSIVENESS PREDICTION DEVICE AND METHOD

TECHNICAL FIELD

The present invention relates to a corrosion prediction device that evaluates and predicts the degree to which a metal will corrode in an environment and a method thereof.

BACKGROUND ART

Infrastructure facilities that support our lives are metal underground facilities in many cases that are used while wholly or partially buried in the ground, as exemplified by steel pipe columns, support anchors and underground steel pipes. These underground facilities are corroded by contact with soil, and deteriorate at different rates depending on the underground environment.

However, since the underground environment is not visible and there has been little accumulation of knowledge, inspection data, and the like related to corrosion therein, it is difficult to quantitatively evaluate the degree of progress in corrosion for each of underground environments. In addition, it is currently difficult to perform prediction with high accuracy.

The progress of corrosion in an underground environment is generally represented by a power law formula ($D=KT^n$) using constants K and n where D is a value related to the amount of corrosion such as a depth of corrosion, and T is a period (a year) for which the metal is exposed to the underground environment. In order to predict the progress of corrosion of a metal buried in an underground environment, the key is how to derive the constants K and n.

For example, a target metal sample may be buried in a certain soil, and taken out after a certain period, and the amount of corrosion thereof may be measured. Then, there is a method of deriving constants K and n by applying the relationship between the number of years of burial and the measured amount of corrosion to the power law formula (Non Patent Literature 1).

CITATION LIST

Non Patent Literature

[NPL 1] Satomi Tsunoda., et al, "Some Problems for Evaluating Soil Aggressivity", Corrosion Engineering, Vol. 36, pp. 168-177 (1987).

SUMMARY OF THE INVENTION

Technical Problem

However, in the above method, since it is necessary to bury the metal sample for at least several years, evaluation takes time. In addition, since results differ greatly depending on the state of the burial environment during the test, and particularly, a state according to which water conditions of soil are controlled, the power law formula is less applicable to facilities in actual environments. That is, the conventional method of deriving a prediction formula according to the power law formula has problems that a long period of at least several years is required and the prediction formula is less applicable to actual environments.

The present invention has been made in view of the above problems, and an object of the present invention is to provide a corrosion prediction device that can derive a prediction formula highly applicable to actual environments by a short-term test as compared with in the related art and a method thereof.

Means for Solving the Problem

A corrosion prediction device according to an aspect of the present invention is a corrosion prediction device that predicts corrosion indicating the degree to which a metal will corrode in an environment, including a storage unit which stores a soil sample that simulates the environment and an electrode unit and has a function of repeatedly performing water supply and drainage with respect to the soil sample; the electrode unit including at least one type of metal; a measurement unit that measures, based on change in water content in the environment in one cycle, a corrosion rate of the metal or a value proportional to the corrosion rate of the metal during the change; a calculation unit that integrates the corrosion rate or a value proportional to the corrosion rate over time and calculates an amount of corrosion or a value proportional to the amount of corrosion; and a prediction unit that determines, based on the amount of corrosion or the value proportional to the amount of corrosion and rainfall information for a predetermined period, a constant value of K of the power law and a constant value of n of the power law using a difference between the amounts of corrosion or the values proportional to the amounts of corrosion in different periods.

In addition, a corrosion prediction method according to another aspect of the present invention is a corrosion prediction method executed by the above corrosion prediction device, the method including a measurement step in which, based on change in water content in one cycle in an environment in which at least one type of metal is disposed, a corrosion rate of the metal or a value proportional to the corrosion rate of the metal during the change is measured; a calculation step in which, based on the value measured in the measurement step, an amount of corrosion of the metal or a value proportional to the amount of corrosion of the metal is calculated; and a prediction step in which, based on the amount of corrosion or the value proportional to the amount of corrosion and rainfall information for a predetermined period, a constant value of K of the power law is determined, and a constant value of n of the power law is determined using a difference between the amounts of corrosion or the values proportional to the amounts of corrosion in different periods.

Effects of the Invention

According to the present invention, it is possible to derive a prediction formula for corrosion progress that is highly applicable to actual environments in a short-term test for a metal object buried in soil.

BRIEF DESCRIPTION OF DRAWINGS

FIG. 8 is a diagram showing an example of an equivalent circuit assumed for calculating a charge transfer resistance.

DESCRIPTION OF EMBODIMENTS

Figure 1:
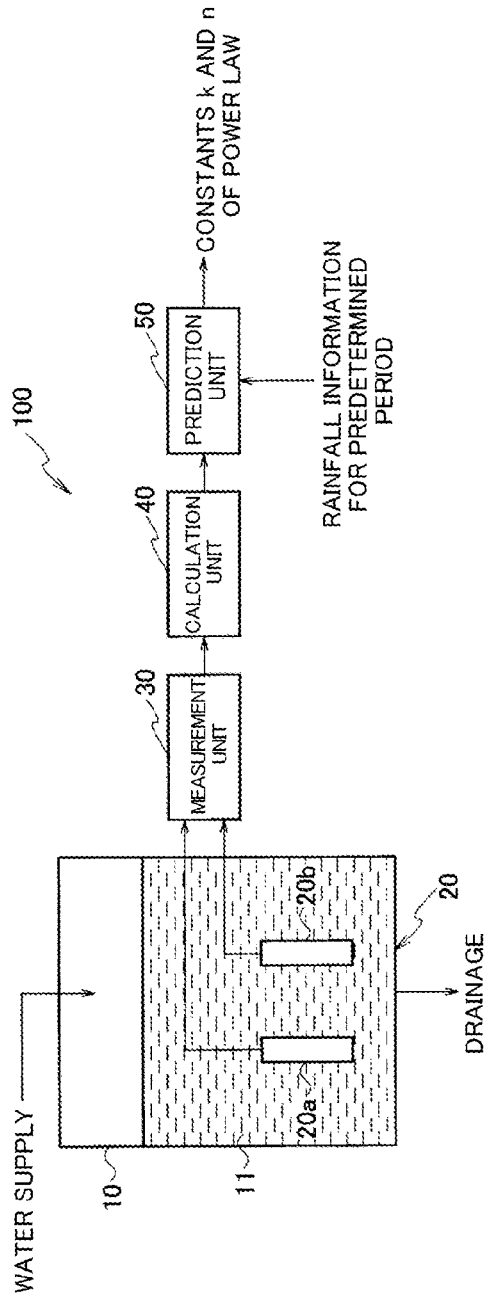
FIG. 1 is a diagram showing a functional configuration example of a corrosion prediction device according to an embodiment of the present invention.

Hereinafter, embodiments of the present invention will be described below with reference to the drawings. The same components in a plurality of drawings are denoted with the same reference numerals and descriptions thereof will not be repeated.

FIG. 1 is a diagram showing a functional configuration example of a corrosion prediction device according to an embodiment of the present invention. A corrosion prediction device 100 shown in FIG. 1 is a device that derives a prediction formula for corrosion progress that is highly applicable to actual environments in a short-term test.

The prediction formula is a power law formula shown in the following formula.

Math. 1

$$D = KT^n \quad (1)$$

Here, D is a value related to the amount of corrosion such as the depth of corrosion. T is a period (for example, a year). Since D=K is obtained when T=1 is defined for Formula (1), the constant K can be considered to correspond to the amount of corrosion in the first year.

Corrosion of a metal buried in soil progresses in an environment in which a wet and dry cycle is repeated with rainfall as a starting point. Therefore, in the present embodiment, first, an electrode containing a metal whose corrosion progress is to be predicted and a soil sample in which the metal is buried are stored in a storage container, and a simulation environment in which water supply and drainage are repeated is constructed. Then, in the simulation environment, the change in the corrosion rate or a value proportional to the corrosion rate over time with respect to one instance of rainfall (water supply), or information about the amount of corrosion or a value proportional to the amount of corrosion obtained by integrating the corrosion rate or a value proportional to the corrosion rate with respect to time is measured and calculated.

Then, in the first year, a value corresponding to the amount of corrosion in the first year is calculated in consideration of the corrosion behavior during one instance of rainfall, which is repeated with rainfall as a starting point. That is, using the corrosion rate or a value proportional to the corrosion rate or the amount of corrosion or a value proportional to the amount of corrosion, the value of K can be calculated cumulatively according to rainfall information for one year at a point where a metal whose corrosion progress is to be predicted is buried or a point where a metal is assumed to be buried.

The value of n is a value related to the attenuation of the amount of corrosion of a target metal with respect to the number of elapsed years. For example, values D1 and D2 related to the amount of corrosion at elapsed times t1 (hour) and t2 (hour) after burial can be expressed by the following formulae.

Math. 2

$$D1 = K \times \left(\frac{t1}{365 \times 24}\right)^n \quad (2)$$

$$D2 = K \times \left(\frac{t2}{365 \times 24}\right)^n \quad (3)$$

The following formula is obtained by taking the ratio between Formula (2) and Formula (3).

Math. 3

$$\frac{D1}{D2} = \frac{(t1)^n}{(t2)^n} \quad (4)$$

Therefore, the value of n is given by the following formula.

Math. 4

$$n = \frac{\{\ln(D1) - \ln(D2)\}}{\{\ln(t1) - \ln(t2)\}} \quad (5)$$

In the present embodiment, the value of n is calculated based on Formula (5).

The corrosion prediction device according to the present embodiment measures the change in corrosion rate of the metal or a value proportional to the corrosion rate over time in an environment in which wetting and drying are repeated due to rainfall up to the elapsed time t1 after burial, and calculates an amount of corrosion or a value D1 proportional to the amount of corrosion at the elapsed time t1. Next, the corrosion prediction device measures the change in corrosion rate of the metal or a value proportional to the corrosion rate over time in an environment in which wetting and drying are repeated due to rainfall up to the elapsed time t2 (t1<t2), and calculates an amount of corrosion or a value D2 proportional to the amount of corrosion at the elapsed time t2. Then, these calculation results are assigned to Formula (5) to calculate the value of n.

When the value of K and the value of n are obtained as described above, a prediction formula that follows the power law is derived.

As shown in FIG. 1, the corrosion prediction device 100 according to the present embodiment includes a storage unit 10, an electrode unit 20, a measurement unit 30, a calculation unit 40, and a prediction unit 50. The electrode unit 20 includes two or more pieces of metal 20a and 20b that are disposed at intervals from each other in the environment.

Figure 2:
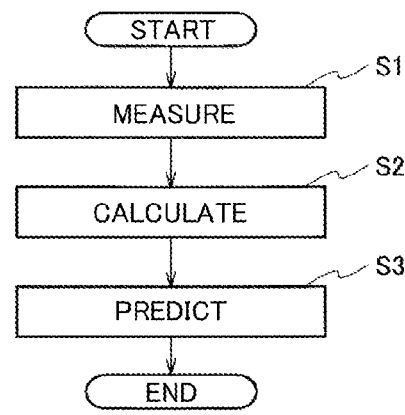
FIG. 2 is a diagram showing an operation flow of the corrosion prediction device shown in FIG. 1.

FIG. 2 is a flowchart showing processing procedures of the corrosion prediction device 100. The operation will be described with reference to FIG. 1 and FIG. 2.

The storage unit 10 shown in FIG. 1 has a function of allowing storage of at least a soil sample 11 and the electrode unit 20 at a target point. In addition, it has a function of repeating the cycle of water supply and drainage to the soil sample 11 at arbitrary time intervals.

The electrode unit 20 is composed of, for example, two metal pieces to be evaluated (the pieces of metal 20a and 20b), and buried in the soil sample 11. The metal pieces 20a and 20b are the same type of metal. That is, the electrode unit 20 is disposed in the environment and contains at least one type of metal. Here, the shape including the size and thickness of the metal pieces 20a and 20b is not particularly limited.

The measurement unit 30 measures, based on the change in water content in the environment in one cycle, a corrosion rate of the metal pieces 20a and 20b during the change or a value proportional to the corrosion rate of the metal pieces 20a and 20b is measured (step S1). The change in water content in one cycle is, for example, a transition of moisture content in the soil from 100% to 0%. Here, the upper limit is not limited to 100%. In addition, the lower limit is not limited to 0%.

The change in water content in the environment in one cycle can be determined by appropriately setting the interval and period during which the corrosion rate is measured. For example, if water is well-drained, it is possible to measure the corrosion rate corresponding to the change in water content in one cycle at a measurement period of about one day and a measurement interval of several hours.

In this example, the environment is soil. The soil is a 3-phase coexistence environment composed of soil particles composed of oxides and the like such as those of Si, Al, Ti, Fe, and Ca and a gas phase and a liquid phase (water) present within the gaps between the soil particles. A total of a proportion of the gas phase and a proportion of the liquid phase in soil can be considered to be constant, and there is a reciprocal relationship in which one proportion increases as the other proportion decreases. In addition, basically water and oxygen are required for a soil corrosion reaction, and corrosion progresses at a corrosion rate that depends on these conditions.

Therefore, the soil moisture content, which indicates the proportion of water in soil, is a major environmental factor that contributes to the corrosion rate, and it can be said that the corrosion rate changes together with the soil moisture content.

The soil moisture content does not always remain constant unless the position is very deep in the ground. For example, the soil moisture content changes according to natural phenomena such as rainfall.

Figure 3:
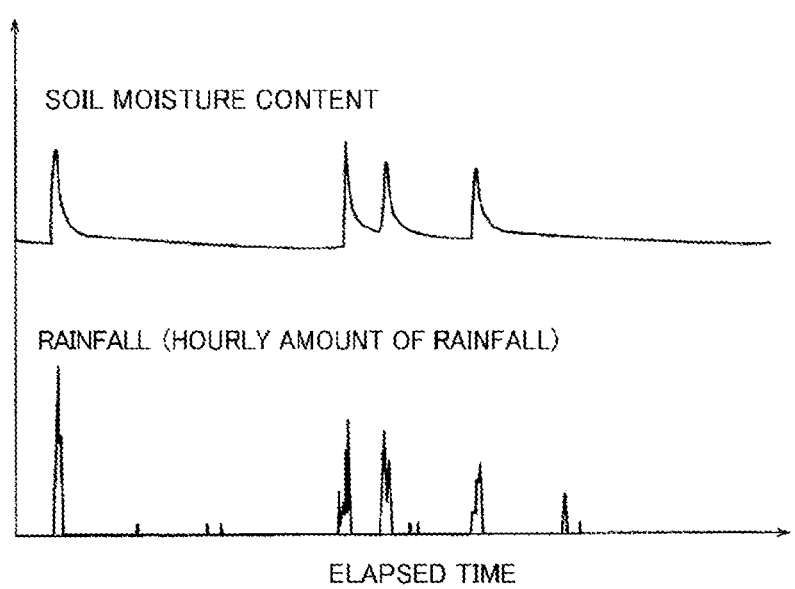
FIG. 3 is a diagram schematically showing the relationship between rainfall and the soil moisture content.

FIG. 3 is a diagram schematically showing the relationship between rainfall and soil moisture content. The horizontal axis in FIG. 3 represents elapsed time. As shown in FIG. 3, the increase or decrease in the soil moisture content is closely linked to rainfall, and repeats a cycle in which it increases rapidly during rainfall and gradually decreases when rain stops. Therefore, it can be considered that the change in corrosion rate over time also repeats a cycle with rainfall as a starting point.

Figure 4:
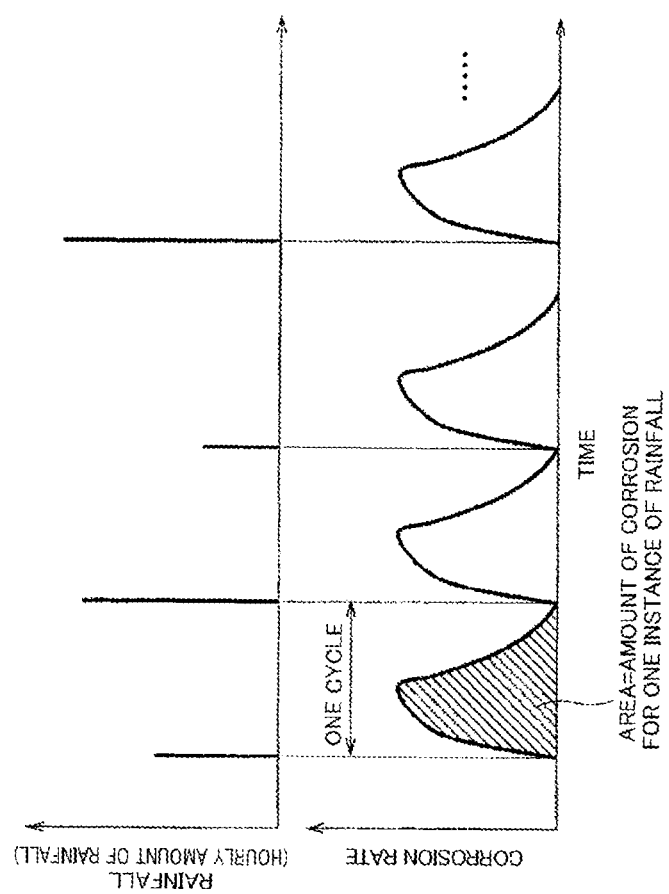
FIG. 4 is a diagram schematically showing the relationship between rainfall and the corrosion rate of a metal in soil.

FIG. 4 is a diagram schematically showing the relationship between rainfall and the corrosion rate of the metal in soil. Here, one cycle is a period from one instance of rainfall to the next rainfall. The length of time in one cycle varies depending on the rainfall interval.

Here, the change in corrosion rate over time in one cycle differs depending on the soil sample 11 and the metal pieces 20a and 20b. In addition, even with the same combination of the soil sample 11 and the metal pieces 20a and 20b, the change in corrosion rate over time differs depending on the number of cycles. For example, in metal pieces such as steel, the change in corrosion rate over time differs between in the 10th cycle and $100^{th}$ cycle from when burial starts, and generally, the corrosion rate decreases as the cycle is continually repeated.

Figure 5:
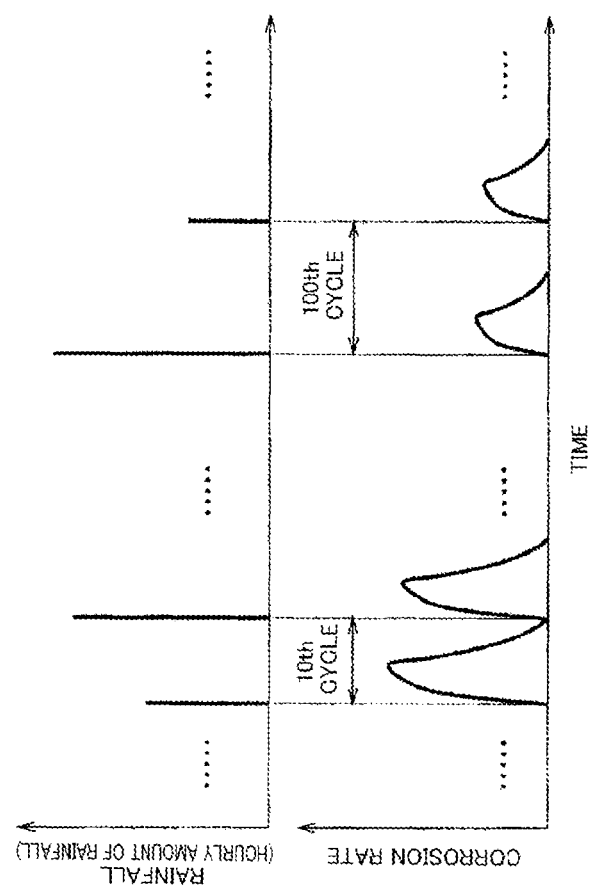
FIG. 5 is a diagram schematically showing the relationship between rainfall and the corrosion rate of a metal in soil when cycles are repeated.

FIG. 5 is a diagram schematically showing the relationship between rainfall and the corrosion rate of the metal in soil when cycles are repeated. As shown in FIG. 5, the corrosion rate decreases as cycles are continually repeated. This is because an oxide film (rust) is formed on the surface of the metal pieces 20a and 20b as corrosion progresses, and the surface rust inhibits the corrosion reaction.

Here, in addition to the soil moisture content, there are many factors that contribute to the corrosion rate. For example, a pH value and an amount of various ions may be exemplified. Since these ion species are basically eluted from soil into water, the pH value and the amount of various ions are uniquely determined if the soil and moisture content are determined. Therefore, it is considered that temporal fluctuations of these factors also cyclically change with rainfall as a starting point.

The measurement unit 30 measures, based on the change in water content in the environment in one cycle, a corrosion rate of the metal pieces 20a and 20b during the change or a value proportional to the corrosion rate of the metal pieces 20a and 20b. A specific measurement method will be described below. Here, while the measurement unit 30 measures the corrosion rate of the metal pieces 20a and 20b of the electrode unit 20 and the like, the corrosion rate is determined by the interaction with the soil sample 11 in which the metal pieces 20a and 20b are disposed. Therefore, the corrosion rate measured by the measurement unit 30 or the like represents the degree of corrosion of the soil sample 11.

The calculation unit 40 integrates the corrosion rate or a value proportional to the corrosion rate over time measured by the measurement unit 30, and calculates an amount of corrosion or a value proportional to the amount of corrosion (step S2). Details will be given below.

The prediction unit 50 determines, based on the amount of corrosion or a value proportional to the amount of corrosion calculated by the calculation unit 40 and rainfall information for a predetermined period, a constant value of K of the power law and a constant value of n of the power law using a difference between the amounts of corrosion or the values proportional to the amounts of corrosion in different periods (step S3).

As described above, the corrosion prediction device 100 according to the present embodiment is a corrosion prediction device that evaluates corrosion indicating the degree to which a metal will corrode in the environment. Here, the corrosion prediction device 100 includes the storage unit 10, the electrode unit 20, the measurement unit 30, the calculation unit 40, and the prediction unit 50. The storage unit 10 stores the soil sample 11 that simulates the environment and the electrode unit 20 and has a function of repeatedly performing water supply and drainage with respect to the soil sample 11. The electrode unit 20 includes at least one type of metal pieces 20a and 20b. The measurement unit 30 measures, based on the change in water content in the environment in one cycle, a corrosion rate of the metal pieces 20a and 20b during the change or a value proportional to the corrosion rate of the metal pieces 20a and 20b. The calculation unit 40 integrates the corrosion rate or a value proportional to the corrosion rate over time and calculates an amount of corrosion or a value proportional to the amount of corrosion. The prediction unit 50 determines, based on the amount of corrosion or a value proportional to the amount of corrosion and rainfall information for a predetermined period, a constant value of K of the power law and a constant value of n of the power law using a difference between the amounts of corrosion or the values proportional to the amounts of corrosion in different periods. Therefore, it is possible to derive a prediction formula for corrosion progress that is highly applicable to actual environments in a short-term test. That is, it is possible to predict corrosion indicating the degree to which a metal will corrode in the environment.

Next, functional components of the corrosion prediction device 100 will be described in detail.

(Storage Unit)

The storage unit 10 has a water supply function of increasing the moisture content of the soil sample 11 and a drainage function of decreasing the moisture content of the soil sample 11. The storage unit 10 stores the soil sample 11 in soil to be evaluated. A storage amount of the soil sample 11 and a form during storage are not particularly limited.

However, it is preferable to secure the storage amount at which the electrode unit 20 can be buried. In addition, the soil sample 11 is a sample of soil in which the metal whose corrosion is to be predicted is buried or the metal is assumed to be buried, and there are no particular limitations on whether it is natural soil or artificial soil, or on its type or collection method.

The water supply function and the drainage function only need to change the moisture content of the soil sample 11 according to the purposes, and the form and method for realizing the functions are not limited. For example, a part of the storage unit 10 may be open, and water may be manually supplied from the part. In addition, drainage may be performed from a part of the storage unit 10.

In addition, automatic water supply and timed water supply may be performed using a pump or the like. The drainage function can be realized by providing a porous filter below the soil sample 11.

(Electrode Unit)

It is necessary for the electrode unit 20 to include as many electrodes as necessary for electrochemical measurement in the measurement unit 30. For example, when AC impedance measurement is performed by a 2-electrode method, as shown in FIG. 1, the metal pieces 20a and 20b are provided. The metal pieces 20a and 20b are directly buried in soil to be evaluated.

In addition, when AC impedance measurement is performed by a 3-electrode method, a working electrode, a counter electrode, and a reference electrode are provided. In this case, platinum, a carbon sheet, or the like are used for the counter electrode, and an Ag/AgCl electrode, a copper sulfate electrode or the like is used for the reference electrode. Here, the AC impedance measurement by the 3-electrode method is well known.

(Measurement Unit)

The measurement unit 30 has at least a measurement function based on an electrochemical measurement method and is electrically connected to the electrode unit 20. The electrochemical measurement method is not particularly limited, and it is preferable to have a measurement function based on an AC impedance method.

When measurement is performed based on the AC impedance method, measurement is performed at arbitrary time intervals. The time interval is not particularly limited, and in consideration of the drainage speed of the soil sample 11, it is preferable to set time intervals so that AC impedance measurement can be performed a plurality of times in one cycle.

In addition, the measurement time and the number of water supply and drainage cycles are not particularly limited, and it is preferable that the number of cycles after the metal pieces 20a and 20b are buried be at least 2 or more. If measurement is performed for about several cycles, the measurement can be completed in about several hours or about several weeks at the longest.

In the AC impedance measurement, metal pieces disposed in the soil sample 11 are used as electrodes, and a weak AC voltage or current is applied between the electrode to measure an electrical response. Here, the metal is not limited to the two metal pieces 20a and 20b as described above.

A voltage or current applied to the metal may be small so that the surface of the metal does not change. For example, the voltage is about ±5 mV. The frequency varies, for example, in a range of 0.1 Hz to several kHz.

Figure 6:
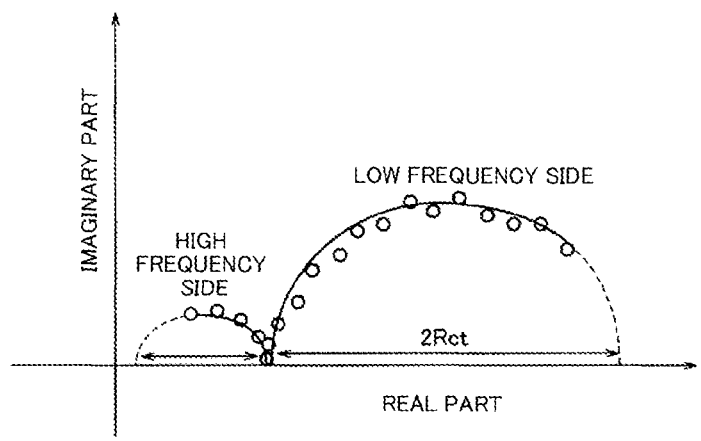
FIG. 6 is a diagram schematically showing a Nyquist diagram.

A Nyquist diagram can be obtained by performing AC impedance measurement. FIG. 6 schematically shows the Nyquist diagram. In the Nyquist diagram, the horizontal axis represents a real part, and the vertical axis represents an imaginary part. Based on the Nyquist diagram, the charge transfer resistance is derived by curve fitting based on a predetermined equivalent circuit.

Figure 7A:
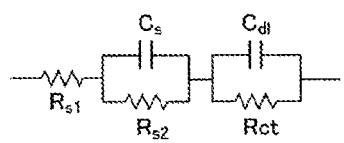
FIG. 7 is a diagram showing an example of an equivalent circuit assumed for calculating a charge transfer resistance.
Figure 7B:
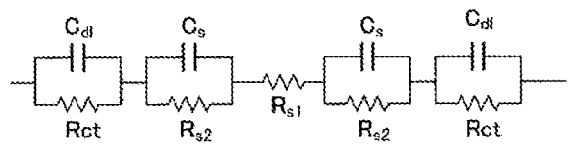

FIG. 7 and FIG. 8 are examples of equivalent circuits assumed to calculate the charge transfer resistance. In both diagrams, (a) shows an equivalent circuit when AC impedance is measured with three electrodes. (b) shows an equivalent circuit when AC impedance is measured with two electrodes.

The charge transfer resistance Rct in the drawing represents the resistance of the corrosion reaction of the metal buried in soil. The electric double layer Cal is a capacitance present at the interface between the metal and soil. The resistance components RS1 and RS2 represent a resistance in soil and another resistance component. The capacitance CS is a capacitance component in soil. The Warburg impedance ZW (FIG. 8) is the impedance due to a diffusion procedure. Here, during curve fitting, the electric double layer Cal and the capacitance CS may be replaced with a constant phase element (CPE).

According to the equivalent circuits shown in FIG. 7 and FIG. 8, as shown in FIG. 6, two arcs are theoretically drawn on the Nyquist diagram. The arc on the high frequency side is derived from soil. The arc on the low frequency side is caused by the corrosion reaction.

The charge transfer resistance Rct is obtained from a width at which the arc on the low frequency side of the Nyquist diagram intersects the horizontal axis (real part). Here, the charge transfer resistance Rct when the AC impedance is measured with two electrodes is a value that is half of the width.

The corrosion rate is proportional to the reciprocal of the charge transfer resistance Rct. The corrosion rate is an ionization amount per unit time on a unit area of the surface of the metal, that is, the same as the current density. The corrosion current density can be obtained by using the reciprocal of the derived charge transfer resistance Rct and the constant of proportionality X based on the principle of the polarization resistance known as the Stern-Geary equation (reference: "Corrosion Monitoring of Metals in Soils by Electrochemical and Related Methods: Part II", Zairyo-to-Kankyo, Vol. 46, pp. 610-619 (1967)).

The constant of proportionality X may be obtained experimentally. The constant of proportionality X is obtained in advance based on results of an anode polarization test and a cathode polarization test for the target metal in soil.

A corrosion current density (corrosion rate) can be calculated from the reciprocal of the charge transfer resistance Rct using the constant of proportionality X. In addition, a value proportional to the corrosion rate such as a rate of weight and thickness loss and a rate of volume and thickness loss may be calculated from the corrosion current density.

Based on the result of one impedance measurement measured in the measurement step (step S1) in this manner, one corrosion rate or a value (1/Rct) proportional to one corrosion rate can be obtained.

(Calculation Unit)

The calculation unit 40 obtains an amount of corrosion or a value proportional to the amount of corrosion of the metal from the values such as the corrosion current density (corrosion rate) or the rate of weight and thickness loss measured by the measurement unit 30. The obtained amount of corrosion or value proportional to the amount of corrosion may be output to the outside.

The calculation unit 40 fits the change in corrosion rate or a value proportional to the corrosion rate over time with the function f(t), and integrates the function f(t) to obtain an amount of corrosion. The corrosion of the soil sample 11 (environment) can be evaluated with the degree of the obtained amount of corrosion.

Figure 9:
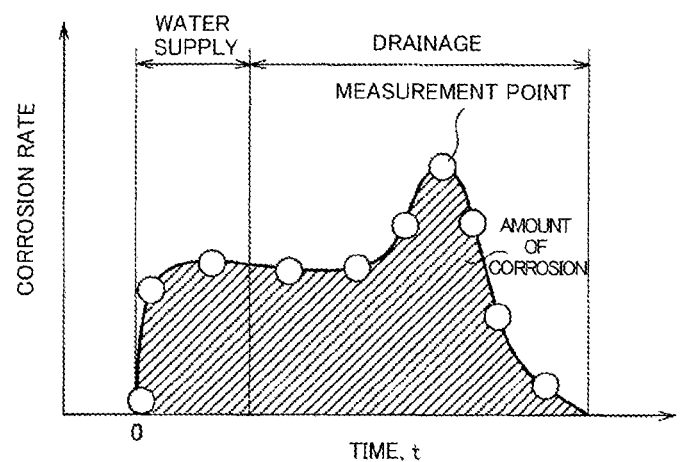
FIG. 9 is a diagram schematically showing the relationship between a time corresponding to the change in water content in one cycle of water supply and drainage and a value (1/Rct) proportional to a corrosion rate.

FIG. 9 is a diagram schematically showing the relationship between a time corresponding to the change in water content in one cycle of water supply and drainage and a value (1/Rct) proportional to the corrosion rate. In FIG. 9, the horizontal axis represents time corresponding to the change in water content in one cycle of water supply and drainage, and the vertical axis represents value (1/Rct) proportional to the corrosion rate.

The area of the shaded part shown in FIG. 9 corresponds to a value proportional to the amount of corrosion. A method of calculating the amount of corrosion or a value proportional to the amount of corrosion is not particularly limited, and a method of simply fitting the change in corrosion rate or a value proportional to the corrosion rate over time with a certain function f(t) and performing calculation by integrating f(t) may be used.

(Prediction Unit)

The prediction unit 50 obtains a constant value of K of the power low from the amount of corrosion or the value (1/Rct) proportional to the corrosion rate and rainfall information for a predetermined period and obtains a constant value of n using a difference between the amounts of corrosion or the value (1/Rct) proportional to the corrosion rate in different periods. The prediction unit 50 preferably obtains the constant value of K and the constant value of n using results of at least two cycles or more obtained by the calculation unit 40. For example, the present embodiment will be described using the results of repeated changes in water content for 5 cycles.

Figure 10:
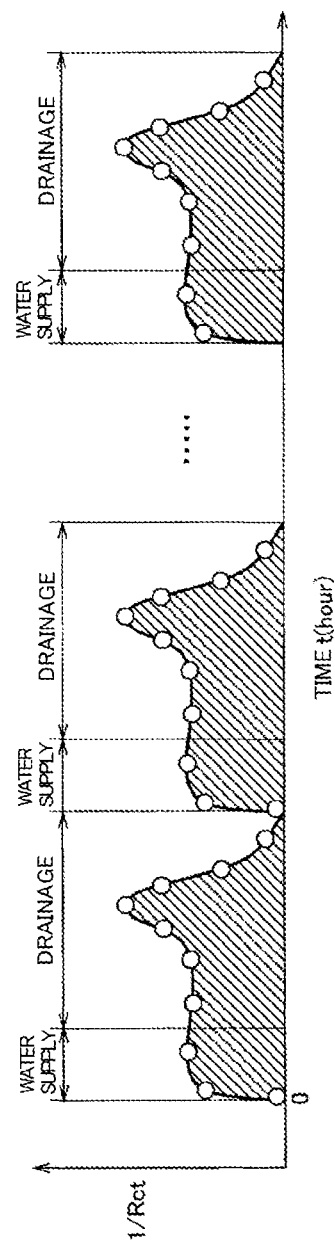
FIG. 10 is a diagram schematically showing the change in a value (1/Rct) proportional to a corrosion rate over time when a cycle of water supply and drainage is repeated at certain time intervals.

FIG. 10 is a diagram schematically showing the change in a value (1/Rct) proportional to the corrosion rate over time when a cycle of water supply and drainage is repeated at certain time intervals.

The constant value of K is calculated cumulatively based on the change in the corrosion rate or a value proportional to the corrosion rate over time in one cycle and rainfall information for one year at a target point. For example, among the results obtained by repeating 5 cycles, the $1^{st}$ cycle may be used.

For rainfall information for one year at the target point, for example, hourly amount of rainfall for the last year may be acquired from public information of the meteorological station. There is no limit to the period for one year acquisition. For example, one year rainfall information regarding the year when prediction starts may be acquired, and when rainfall information for one year is not obtained, any rainfall information may be acquired.

Figure 11:
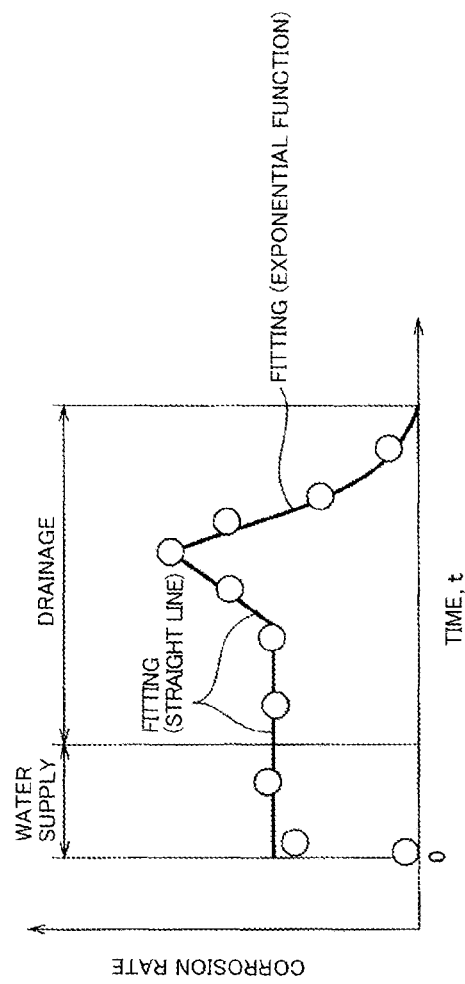
FIG. 11 is a diagram schematically showing an example of a fitting function.

For example, the change in corrosion rate or a value proportional to the corrosion rate over time is fitted with the function f(t). The function f(t) is not particularly limited. For example, as shown in FIG. 11, a function formed of two straight lines and one exponential function may be used.

When it is assumed that hourly amount of rainfall for one year is acquired as rainfall information for one year at the target point, the corrosion rate or a value proportional to the corrosion rate over one year assuming that the function f(t) is repeated for each rainfall is calculated based on the hourly rainfall. The corrosion rate or a value proportional to the corrosion rate over one year corresponds to the constant value of K of the power law.

The constant value of n is calculated using a difference between the amount of corrosion or a value proportional to the amount of corrosion up to an arbitrary elapsed time t1 and the amount of corrosion or a value proportional to the amount of corrosion up to an elapsed time t2 longer than the arbitrary elapsed time t1. That is, for example, the elapsed time when the second cycle is completed is set as t1, and the amount of corrosion or a value D1 proportional to the amount of corrosion up to the elapsed time t1 is calculated by integrating the amount of corrosion or a value proportional to the amount of corrosion up to the second cycle with respect to time.

Next, for example, the elapsed time up to the $5^{th}$ cycle is set as t2, and the amount of corrosion or a value D2 proportional to the amount of corrosion up to the elapsed time t2 is calculated by integrating the amount of corrosion or a value D2 proportional to the amount of corrosion up to the $5^{th}$ cycle with respect to time.

D1 and D2 calculated as described above and t1 and t2 are assigned to Formula (5) to obtain the value of n. The value of K and the value of n forma prediction formula for the power law. One prediction formula can be set for the target soil and metal.

Here, in a combination of the soil and metal of the same type, measurement by the measurement unit 30 can be omitted, and the prediction formula can be derived only from rainfall information at the target point. In addition, it is possible to obtain a prediction formula under assumed conditions, and predict the amount of corrosion under those conditions.

Here, it is preferable to store the result of the change in corrosion rate or a value proportional to the corrosion rate over time once measured and to be configured so that it can be used at any time. The calculation unit 40 and the prediction unit 50 configured in this manner can be easily realized in a personal computer or the like.

(Modified Example of Storage Unit)

The storage unit 10 may include an environment function unit that simulates an environment to be evaluated. Regarding the environment function unit, for example, a temperature control function unit (not shown) and an oxygen concentration control function unit may be considered.

The temperature control function unit is, for example, a constant temperature chamber, and when the storage unit 10 is put into a constant temperature chamber, the temperature of the environment to be evaluated can be simulated.

The oxygen concentration control function unit can be realized by providing a space in which the surface of the soil sample 11 is exposed to a gas in the storage unit 10. An intake port for introducing a gas and an exhaust port for discharging a gas are provided in the space, and for example, a mixed gas of $N_2$ and $O_2$ is introduced. In addition, $CO_2$ may be mixed.

Figure 12:
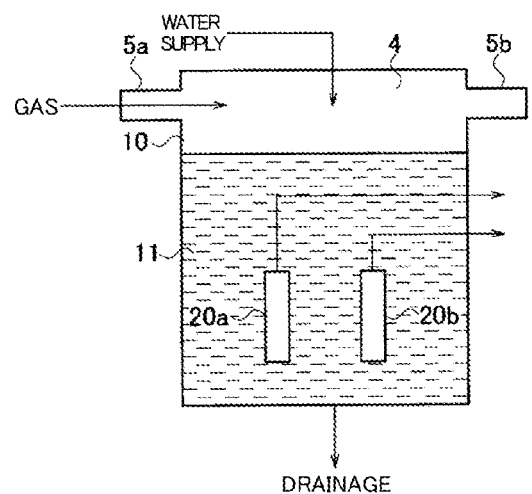
FIG. 12 is a diagram schematically showing an example of a storage unit including a space in which the surface of a soil sample is exposed to a predetermined gas.

FIG. 12 is a diagram schematically showing an example of the storage unit 10 including a space 4 in which the surface of the soil sample 11 is exposed to a predetermined gas. A gas is introduced from an intake port 5a and discharged from an exhaust port 5b. The concentration of oxygen in a soil sample 3 can be controlled by using, for example, the above mixed gas as the gas and changing the ratio thereof. That is, the space 4, the intake port 5a, and the exhaust port 5b shown in FIG. 12 constitute an oxygen concentration control function unit. Thereby, a simulation environment close to the actual soil environment can be created, and reliability of corrosion evaluation can be improved.

Here, the storage unit 10 has been described with an example in which the soil sample is stored, but it is not limited to this example. The storage unit 10 may store only a gas or may store two phases of a liquid and a gas. When only a gas is stored, the soil moisture content is the humidity in the storage unit 10.

Thus, the water content in the environment is not limited to the soil moisture content. For example, when two phases of a liquid and a gas are stored in the storage unit 10, the water content in the environment is the proportion (amount) of the metal pieces 20a and 20b immersed in the liquid, or the number of times that the surface of the metal pieces 20a and 20b is exposed to the liquid. That is, the change in water content in the environment in one cycle means a one-cycle change in water-related amounts such as water content, water film thickness, and humidity of the surface of the metal disposed in the environment.

The storage unit 10 encloses a simulation of the environment in which corrosion is to be evaluated. That is, the corrosion prediction device 100 includes the storage unit 10 in which the electrode unit 20 is stored. Thus, the measurement unit 30 measures, based on the change in moisture content in the storage unit 10 in one cycle, for example, the corrosion rate of the metal pieces 20a and 20b, or for example, the value proportional to the corrosion rate of the metal pieces 20a and 20b, during the change. Thereby, it is possible to evaluate corrosion in the environment in the laboratory and it is possible to derive a prediction formula for corrosion progress that is highly applicable to actual environments in a short-term test.

As described above, according to the corrosion prediction device 100 of the present embodiment, it is possible to derive a prediction formula for corrosion progress. Here, while soil has been described as the environment described in the above embodiment, the present invention is not limited thereto.

The environment may be in air or in water. When the electrode unit 20 is disposed in the environment, it is possible to quantitatively evaluate corrosion in each environment with an accuracy according to the actual situation.

The present invention is not limited to the above embodiment, and can be modified within the spirit and scope thereof. For example, while the electrode unit 20 composed of two metal pieces 20a and 20b that are disposed at intervals from each other has been exemplified, an electrode unit including three electrodes: a counter electrode, a working electrode, and a reference electrode may be used.

As described above, of course, the present invention includes various embodiments and the like that are not described here. Therefore, the technical scope of the present invention is defined only by the matters specifying the invention related to appropriate claims from the above description.

REFERENCE SIGNS LIST

100 Corrosion prediction device
10 Storage unit
11 Soil sample
4 Space (environment function unit)
20 Electrode unit
20a, 20b Metal piece
30 Measurement unit
40 Calculation unit
50 Prediction unit

The invention claimed is:

1. A corrosion prediction device that predicts corrosion indicating the degree to which a metal will corrode in an environment, the device comprising:
    a storage unit which stores a soil sample that simulates the environment and an electrode unit and has a function of repeatedly performing water supply and drainage with respect to the soil sample;
    the electrode unit including at least one type of metal;
    a measurement unit that measures, based on change in water content in the environment in one cycle, a corrosion rate of the metal or a value proportional to the corrosion rate of the metal during the change;
    a calculation unit that integrates the corrosion rate or a value proportional to the corrosion rate over time and calculates an amount of corrosion or a value proportional to the amount of corrosion; and
    a prediction unit that determines, based on the amount of corrosion or the value proportional to the amount of corrosion and rainfall information for a predetermined period, a constant value of K of a power law and a constant value of n of the power law using a difference between the amounts of corrosion or the values proportional to the amounts of corrosion in different periods.

2. The corrosion prediction device according to claim 1, wherein the storage unit has an environment function unit that simulates the environment to be evaluated.

3. A corrosion predicting method executed by a corrosion prediction device that predicts corrosion indicating the degree to which a metal will corrode in an environment, the method comprising:
    a measurement step in which, based on change in water content in one cycle in an environment in which at least one type of metal is disposed, a corrosion rate of the metal or a value proportional to the corrosion rate of the metal during the change is measured;
    a calculation step in which the corrosion rate or a value proportional to the corrosion rate measured in the measurement step is integrated over time, and an amount of corrosion or a value proportional to the amount of corrosion is calculated; and
    a prediction step in which, based on the amount of corrosion or the value proportional to the amount of corrosion and rainfall information for a predetermined period, a constant value of K of a power law is determined, and a constant value of n of the power law is determined using a difference between the amounts of corrosion or the values proportional to the amounts of corrosion in different periods.

* * * * *